United States Patent [19]

Traitler et al.

[11] Patent Number: 5,474,775
[45] Date of Patent: Dec. 12, 1995

[54] COSMETIC COMPOSITIONS CONTAINING 2,3-BUTANEDIOL FATTY ACID DIESTERS

[75] Inventors: Helmut Traitler, Corseaux; Jean-Louis Viret, Brent, both of Switzerland

[73] Assignee: Nestec S.A., Vevey, Switzerland

[21] Appl. No.: 994,275

[22] Filed: Dec. 21, 1992

[30] Foreign Application Priority Data

Jan. 8, 1992 [EP] European Pat. Off. ............. 92100208

[51] Int. Cl.$^6$ .................. A61K 6/00; A61K 7/00
[52] U.S. Cl. ................ 424/401; 424/63; 424/70.9; 424/70.11
[58] Field of Search ............... 424/401, 72, 63; 514/374, 169; 252/351

[56] References Cited

U.S. PATENT DOCUMENTS

| | | | |
|---|---|---|---|
| 3,600,186 | 8/1971 | Mattson et al. | 426/611 |
| 3,959,321 | 5/1976 | McKenna III | 260/398.5 |
| 4,080,465 | 3/1978 | Bouillon et al. | 424/72 |
| 4,504,409 | 3/1985 | Tsutsumi et al. | 252/351 |
| 4,557,934 | 12/1985 | Cooper | 514/374 |
| 4,767,741 | 8/1988 | Komor | 424/401 |
| 4,954,487 | 9/1990 | Cooper et al. | 514/159 |
| 5,006,351 | 4/1991 | Klemann et al. | 426/611 |
| 5,008,126 | 4/1991 | Klemann et al. | 426/611 |
| 5,061,700 | 10/1991 | Dow et al. | 514/169 |
| 5,080,889 | 1/1992 | Katada et al. | 424/63 |

FOREIGN PATENT DOCUMENTS

| | | |
|---|---|---|
| 61114A2 | 11/1985 | European Pat. Off. . |
| 05874A1 | 1/1991 | European Pat. Off. . |
| 65689A1 | 1/1992 | European Pat. Off. . |

OTHER PUBLICATIONS

Mattson, et al. "Hydrolysis of fully esterified alcohols containing from one to eight hydroxyl groups by the lipolytic enzymes of rat pancreatic juice"; Journal of Lipid Research, 1972 vol. 13, pp. 325–328.

Wille et al. "Wiederveresterung von Konzentraten mehrfach ungesättigter Fettsäuren"; Fat. Sci. Techol., 89(12): 1987, pp. 480–485; and translation thereof.

*Primary Examiner*—Gollamudi S. Kishore
*Assistant Examiner*—William E. Benston, Jr.
*Attorney, Agent, or Firm*—Vogt & O'Donnell

[57] ABSTRACT

Cosmetic compositions in the form of oil-in-water emulsions, water-in-oil emulsions and anhydrous formulations have fatty phases which contain fatty acid diesters of 2,3-butanediol.

17 Claims, No Drawings

COSMETIC COMPOSITIONS CONTAINING 2,3-BUTANEDIOL FATTY ACID DIESTERS

BACKGROUND OF THE INVENTION

This invention relates to a cosmetic or dermatological composition containing a diester of 2,3-butanediol and a fatty acid, more particularly a $C_{16-22}$ fatty acid, as a viscosity agent and emollient.

In cosmetic or dermatological compositions containing a fatty phase of the emulsion type or anhydrous type, esters, hydrocarbons and glycerides are often used as viscosity agents and emollients.

The principal requirements which these compounds are expected to satisfy are as follows:

- they should be miscible in virtually any ratio with the esters, fats and liposoluble vitamins commonly used for cosmetic and galenic purposes,
- they should preferably be colourless and substantially odourless,
- their dissolving power should enable them to act as a vehicle for liposoluble active principles,
- they should preferably be readily emulsifiable,
- they should not adversely affect the rheological properties, particularly the viscosity and thixotropy, of the end products, and
- they should have good sensorial or organoleptic qualities, i.e., they should impart to the end products a pleasant sensation on the skin, for example through their ready spreadability.

SUMMARY OF THE INVENTION

It has been found that diesters of 2,3-butanediol and fatty acids, more particularly $C_{16-22}$ fatty acids, show the properties mentioned above to a remarkable degree.

DETAILED DESCRIPTION OF THE INVENTION

The above-mentioned compounds which enter into the composition according to the invention and a process for their production are described in patent application European Patent Application Publication No. 0 465 689, wherein it is disclosed that the fatty acid diesters of 2,3-butanediol may be prepared in a known manner, by chemical esterification of the polyol with a fatty acid or fatty acid mixture in the absence of an organic solvent, this method having been applied to the re-esterification of fatty acids with glycerol described, for example, in Fat. Sci. Technol. 89, 480–485. The esterification reaction takes place in a reactor equipped with a stirrer, with means for keeping the temperature at a value close to the reflux temperature of the mixture of reactants and with means for removing the water of reaction by distillation. The reaction is carried out in the presence of a catalyst, for example zinc chloride, with a slight excess of polyol over a period of 2 to 4 h at 150° to 170° C. A vacuum of 2.7 to 27 mb (2 to 20 mm Hg) is then applied and distillation is continued for 1 to 3 h.

After cooling to ambient temperature, the mixture is taken up in a solvent, for example hexane, and the zinc chloride is separated by filtration. The product obtained may then be purified by chromatography, for example on alumina. Alternatively, the mixture is directly subjected, i.e., without being taken up in a solvent, to refining without degumming, i.e., by neutralization, decoloration, evaporation of the solvent and, finally, deodorization.

In a variant of the synthesis, the esterification may again be carried out in known manner by the enzymatic method using a non-specific lipase, for example of yeast. A lipase of *Candida cylindracea,* for example, may thus be used. This is done by a batch process in which the fatty acids are dissolved in a hydrocarbon, for example n-heptane or n-hexane, for example in a concentration by weight of 2 to 10%. The polyol is mixed with approximately 10% water containing an excess of enzyme in relation to the fatty acids, for example approximately 3 parts by weight enzyme to 2 parts by weight fatty acid. The aqueous phase (pH approx. 7.2) and organic phase are introduced with vigorous stirring at a temperature of 20° to 55° C. and preferably at a temperature of 40° to 45° C. The reaction—in heterogeneous medium—takes place at the interface between the two phases and is displaced towards the formation of ester because the ester passes into the organic phase as it is produced.

In one preferred continuous variant of this enzymatic synthesis, the reactants may be introduced into an enzyme immobilized, for example, on resin, silica or cloth in a reactor which enables a smaller quantity of enzyme to be used.

The nature of the constituent fatty acid(s) of the esters and their proportions are dictated by the physicochemical, chemical stability and sensorial properties required for a particular cosmetic application. Accordingly, the fatty acids are preferably saturated types, such as palmitic, myristic, stearic and lauric acid, and mono-unsaturated or di-unsaturated types, such as oleic and linoleic acid, with a predominance of oleic, stearic and palmitic acids.

Thus, if the ester predominantly contains oleic acid for example, it will be present in the form of an oil at ambient temperature, for example 20° C., with essentially emollient properties, i.e., with a smoothing and softening effect on the skin. If the ester predominantly contains saturated fatty acids, for example stearic and palmitic acid, it will be in the form of a crystallized solid at 20° C. and, in addition, will act as a viscosity agent by virtue of its consistency.

The preferred compounds mentioned above may be used in virtually any water-based cosmetic or galenic preparations, such as, for example, creams, milks, shampoos in the form of water-in-oil or oil-in-water emulsions, or anhydrous formulations such as, for example, bath oils, massage oils, sun oils, balms, foundations and lipsticks.

A composition according to the invention preferably contains 0.5 to 80% by weight of the diester defined above.

In such a composition, the fatty phase may contain animal, vegetable, mineral or synthetic oils. It may also contain waxes, long-chain alcohols, thickening or gelling agents. Where it is in the form of an emulsion, a cosmetic composition may contain 1 to 20% by weight of an emulsifier, and may contain from 0.5% to 20% be weight diesters, based on the weight of the composition.

In an anhydrous cosmetic composition, the fatty phase may contain 10 to 80% by weight and preferably 10 to 40% by weight diester, based on the total weight of the composition. In addition, it may contain oils and a relatively high proportion, for example 5 to 30% by weight, of waxes. It may be formulated, for example, as a sunscreen oil (in which case it contains a filter to absorb ultraviolet rays).

In addition, a composition according to the invention may contain various additives, more particularly colourants, perfumes, preservatives, ultraviolet filters, pearlescers and mineral or organic fillers. Advantageously, it contains antioxidants in a quantity of 0.02 to 0.2% by weight.

EXAMPLES

The invention is illustrated by the following Examples in which parts and percentages are by weight, unless otherwise indicated.

The nomenclature used in the Examples is the nomenclature of the Cosmetic, Toiletry and Fragrance Association, Inc., Washington D.C. (CTFA).

To prepare the emulsions, the components of the lipidic phases A and, optionally, B are separately mixed and heated to 70° C., after which phase B is optionally incorporated in phase A. The aqueous phase C is prepared by mixing its components and heating to 70° C. The lipidic phase(s) A and, optionally, B is/are added to the aqueous phase C (in the case of oil-in-water emulsions) at 70° C. while stirring at average speed (in the case of water-in-oil emulsions, the aqueous phase is added to the lipidic phase(s)). The mixture of the two phases is homogenized, stirred at approximately 100 r.p.m. and then left to cool to 45°–50° C. in the case of water-in-oil emulsions and to 35°– 40° C. in the case of oil-in-water emulsions.

The additives are then optionally added at that temperature, after which cooling is continued to ambient temperature with slow stirring, stirring being stopped when the product is semifluid (at approx. 25° C.).

The anhydrous products are obtained in the same way, but without homogenization, by hot mixing (at approx. 70° C.) and gradual cooling with slow stirring.

This procedure is applied in the Examples by default. Where a different procedure is followed, it is specifically indicated.

In Examples 1–2, a sensorial method is used to evaluate the organoleptic characteristics of the diol diesters when they are applied to the skin from a lotion in the form of an oil-in-water emulsion.

The dynamic viscosity (at maximum shear in mPa) and the thixotropy of the lotions are also evaluated. Thixotropy is determined from the flow curve (rheogram, shear force as a function of the shear rate) as the area between the ascending curve and the descending curve, expressed in Pa. The viscosity and thixotropy measurements are carried out at 20° C. using a CONTRAVES RHEOMAT 115®.

Method

A. Definition

This method enables the various characteristics which define the feel of cosmetic and galenic products to be numerically quantified by an index (FI, feel index).

The feel index comprises three parameters, namely:

1. The initial feel composed of:

a texture mark of 1 (too watery, poor) to 5 (unctuous, very rich) and a slip mark of 1 (excessive blocking) to 5 (slips well), the score representing the average of the two marks.

2. The intermediate feel during spreading which comprises:

a spreading mark of 1 (excessive blocking) to 5 (slips well), a mark determining the break or the change of texture of 1 (becoming clearly watery) to 5 (no change), a tackiness mark of 1 (too tacky) to 5 (not tacky), a penetration rate mark of 1 (unsatisfactory) to 5 (optimal) and a degree of penetration mark of 1 (non-existent or poor) to 5 (very good), the score representing the average of the five marks.

3. The final feel after complete evaporation of the volatile compounds comprising:

a mark defining the impression on rubbing of 1 (excessive blocking) to 5 (slips well), a mark characterizing the residual lipidic film on the skin of 1 (non-existent, dry skin) to 5 (rich, skin well nourished) and a skin softness mark of 1 (rough) to 5 (velvety, very soft), the score being the total of the three marks.

The feel index is expressed as the initial feel score/total of the intermediate feel and final feel scores.

B. Experimental Part

The test is based on the comparison of an experimental formulation containing the substance to be tested and a control formulation serving as reference for assigning the scores, the control formulation having the following composition:

|  |  | % |
|---|---|---|
| PHASE A (lipidic) |  | 10.1 |
| PEG-10 isocetyl ether monostearate | 4.5 |  |
| STEARETH-21 | 1.5 |  |
| Glycerol stearate | 2.6 |  |
| Cetearyl alcohol | 1.5 |  |
| PHASE B (lipidic) |  | 6.3 |
| Paraffin oil | 6.0 |  |
| CARBOMER 934 (polycrosslinked acrylic acid polymer) | 0.3 |  |
| PHASE C (aqueous) |  | 81.8 |
| Water | 76.7 |  |
| Glycerol | 5.0 |  |
| Ethylenediamine tetra-acetate (EDTA) | 0.1 |  |
| ADDITIVES |  | 1.8 |
| Phenoxy parabene | 0.6 |  |
| Silmethicone | 0.1 |  |
| Trimethamine (30% aqueous solution) | 0.8 |  |
| Perfume | 0.3 |  |
|  |  | 100 |

This formulation (hereinafter referred to as "comparison 1") was developed to obtain a reference FI value. This mean value can increase or decrease in accordance with the quality of the substance(s) to be tested which is/are incorporated in this formulation instead of the 6% paraffin oil. In the case of Example 2, 10% of the compound is incorporated, the glycerol stearate and cetearyl alcohol both being omitted.

The samples of lotions to be tested are presented to the testers in groups of 4 to 6 which corresponds to the maximum number that can be tested per test session.

The product is applied to the insides of the forearms. The quantity of product to be applied should be the same for each test, i.e., approximately 0.2 g.

The samples are tested "blind". Each tester records his or her feelings from the application of the product to its drying on the skin. The marks are recorded in the order of the questionnaire. On completion of the test, the name of the product is revealed to the testers.

It is possible by this method to quantify the feel of any cosmetic product applied to the skin and to do so in a reasonably reproducible manner both in cases where the tester repeats his or her own tests at various time intervals and when he or she repeats the tests of another tester.

The products to be tested are as follows:

Example 1

56.4 g of a mixture of fatty acids containing:

|  | % |
|---|---|
| oleic acid | 70 |
| stearic acid | 10 |
| palmitic acid | 10 |
| linoleic acid | 5 |
| myristic, palmitoleic and arachic acids | 5 | are mixed with 0.56 g zinc chloride in a reactor equipped with a stirrer and the mixture is heated with stirring to 160° C. The reactor is purged with nitrogen during the heating phase. 9 g 2,3-butanediol in racemate form are then gradually added with stirring. The reactor is provided with a descending condenser kept at 15° C. by circulation of cold water. After a reaction time of 3 h at 160° C., a vacuum of 5 mb is applied and the water is continuously eliminated with the remaining 2,3-butanediol by evaporation over a period of 2 h. After purification of the liquid obtained by passage of a 1:1 solution in hexane over a column of aluminum oxide, a purified ester is collected having the following physiochemical properties:

Appearance: Colourless and substantially odourless oily liquid

Refractive index: 1.4635

Free fatty acids (%): 0.05–1

Dynamic viscosity (mPa): 49

Density at 22° C.: 0.895

Example 2

2 Mol of a mixture of fatty acids containing:

|  | % |
|---|---|
| lauric acid | 13 |
| stearic acid | 33 |
| palmitic acid | 23 |
| oleic acid | 28 |
| other acids | 3 | is heated with 1% zinc chloride with stirring at 160° C. and 1.15 mol 2,3-butanediol (racemate) is gradually added. The mixture is left to react at that temperature for 3 h, during which the water formed is continuously removed in the form of steam. A vacuum of 13 mb (10 mm Hg) is then applied and the reaction is continued under these conditions for 2 h. After cooling to ambient temperature, the zinc chloride is separated by filtration. After neutralization, decoloration and, finally, deodorization, a composition is collected having the following physiochemical properties:

Appearance at 20° C.: White crystalline solid

Appearance at 50° C.: colourless and substantially odourless oily liquid

Melting point: Around 40° C.

Other products than paraffin oil which represent the various classes of emollients typically used for this purpose in cosmetics are used as comparison emollients:

Comparison 2: octyl palmitate,

Comparison 3: caprylic and capric acid triglyceride

Comparison 4: diisopropyl adipate

Comparison 5: isodecyl laurate

Comparison 6: isopropyl myristate

Comparison 7: oleyl oleate

Comparison 8: oleic alcohol

Comparison 9: squalene

Results

The FI values and the dynamic viscosity (mPa) and thixotropy (Pa) of the lotions are set out in Table 1 below:

TABLE 1

| | Characteristics of the lotions | | |
|---|---|---|---|
| Compound | FI | Viscosity | Thixotropy |
| Example 1 | 4.5/18 | 2226 | 1400 |
| Example 2 | 4.5/14 | 1711 | 2236 |
| Comparison 1 | 3.5/16 | — | — |
| Comparison 2 | 4.5/18.5 | 1734 | 1852 |
| Comparison 3 | 3.5/15 | 1958 | 1773 |
| Comparison 4 | 3.5/18 | 2399 | 2743 |
| Comparison 5 | 4/13 | 1801 | 2128 |
| Comparison 6 | 4.5/17.5 | 1829 | 1877 |
| Comparison 7 | 4/15 | 1801 | 1368 |
| Comparison 8 | 4/11.5 | 2668 | 2601 |
| Comparison 9 | 4/17.5 | 1409 | 1573 |

These results illustrate the organoleptic qualities of the compounds suitable for use in accordance with the invention:

By comparison with the representatives of the various classes of emollients, the compounds of Examples 1 and 2 impart a rich initial feel (satiny impression) and an extremely pleasant sensation on the skin by virtue of their excellent spreading property.

The compound of Example 1 in particular achieves the best score while the FI value of the compound of Example 2 represents a very good average and, in any event, is very much better than that of such compounds as the fatty alcohols and triglyceride fractions also used as viscosity agents (comparisons 3 and 8).

So far as the rheological properties are concerned, the compound of Example 1 has advantages over the majority of emollients tested. This is because the incorporation of esters or triglycerides always modifies the viscosity of the formulations and this modification has to be compensated by the addition of such products as fatty alcohols and triglyceride fractions which have an adverse effect on feel. In addition, its thixotropy is very satisfactory so that there is no need to add regulators.

In addition, the compound of Example 2 (or the other esters of 2,3-butanediol with saturated fatty acids of high boiling point, such as myristic acid, palmitic acid and stearic acid) may be successfully used as a viscosity agent and emollient. Its viscosity is satisfactory despite the absence of viscosity agents, such as cetearyl alcohol and glycerol stearate.

Examples 3–9

3. Cleansing Milk (Oil-in-Water Emulsion)

|  |  | % |
|---|---|---|
| PHASE A (lipidic) |  | 21.55 |
| Compound of Example 1 | 7 |  |
| 2-Ethylhexyl-2-ethylhexanoate | 3 |  |
| Glyceryl tri-$C_{10-18}$ acids | 4 |  |
| Paraffin oil | 3 |  |
| Glycerol stearate | 3 |  |
| Stearic acid | 1.5 |  |
| Tocopherol, butylhydroxyanisole (BHA) and triethyl citrate | 0.05 |  |
| PHASE C (aqueous) |  | 48.07 |
| Water | 47.88 |  |
| Tetrahydroxypropyl ethylenediamine | 0.14 |  |
| EDTA disodium salt | 0.05 |  |
| ADDITIVES |  | 30.38 |
| Hydroxyethyl cellulose (2% aqueous solution) | 30 |  |
| Methyl chlorothiazolinone and methyl isothiazolinone | 0.08 |  |
| Perfume | 0.3 |  |
|  |  | 100 |

4. Moisturizing Cream (Oil-in-Water Emulsion)

|  |  | % |
|---|---|---|
| PHASE A (lipidic) |  | 26.05 |
| PEG-8-$C_{12-18}$ alkyl ester | 10 |  |
| Compound of Example 1 | 7 |  |
| Isodecyl laurate | 5 |  |
| Cetearyl alcohol | 4 |  |
| Tocopherol, BHA and triethyl citrate | 0.05 |  |
| PHASE C (aqueous) |  | 73.67 |
| Water | 62.67 |  |
| PEG-5-$C_{12-18}$ alcohols | 2 |  |
| Propylene glycol | 5 |  |
| Panthenol | 2 |  |
| Sodium PCA | 2 |  |
| ADDITIVES |  | 0.28 |
| Perfume | 0.2 |  |
| Methyl chlorothiazolinone and methyl isothiazolinone | 0.08 |  |
|  |  | 100 |

5. Skin-care Cream (Water-in-Oil Emulsion)

|  |  | % |
|---|---|---|
| PHASE A (lipidic) |  | 39 |
| PEG-1 glyceryl oleostearate and paraffin wax | 12 |  |
| Paraffin oil | 13 |  |
| Compound of Example 1 | 8 |  |
| Caprylic and capric acid triglycerides | 5 |  |
| 2-Phenoxyethanol, methyl parabene, ethyl parabene, propyl parabene and butyl parabene | 1 |  |
| PHASE C (aqueous) |  | 60.8 |
| Water | 58.1 |  |
| Magnesium sulfate heptahydrate | 0.7 |  |
| Glycerol | 2 |  |
| ADDITIVE |  | 0.2 |
| Perfume | 0.2 |  |
|  |  | 100 |

6. Oil for the Face and Body (Anhydrous)

|  | % |
|---|---|
| Mineral oil | 56.85 |
| Compound of Example 1 | 10 |
| Octyl octanoate | 10 |
| $C_{10-18}$ Fatty acid triglycerides | 10 |
| Cyclomethicone | 5 |
| Isodecyl laurate | 5 |
| Octyl methoxycinnamate | 3 |
| Perfume | 0.1 |
| Tocopherol, triethyl citrate and BHA | 0.05 |
|  | 100 |

7. Anhydrous Balm

|  | % |
|---|---|
| Paraffin | 4 |
| Ozocerite | 5 |
| 2-Ethylhexyl-2-ethyl hexanoate | 45.6 |
| Compound of Example 1 | 40 |
| Isodecyl laurate | 5 |
| Tocopherol, triethyl citrate and BHA | 0.1 |
| Perfume | 0.3 |
|  | 100 |

The components are mixed at approximately 75° C.

8. Medicated Shampoo (Oil-in-Water Emulsion)

|  | % |
|---|---|
| PHASE A (lipidic) |  |
| Cocoamphoglycinate | 10 |
| Ammonium laureth sulfate | 7 |
| Ammonium lauryl sulfate | 3 |
| Cocoamidopropyl betaine | 2 |
| Compound of Example 1 | 0.5 |
| Panthenol | 0.5 |
| PHASE B (aqueous) |  |
| Water | 68.9 |
| Acrylates/STERETH-20 methacrylate copolymer | 4 |
| Hydroxypropyl methyl cellulose | 2 |
| Polysorbate | 1 |
| QUATERNIUM 23 (quaternized polymers) | 0.5 |
| Citric acid | 5.65 |
| Methyl dibromoglutaronitrile and 2-phenoxyethanol | 0.20 |
|  | 100 |

The components of phase A are mixed at ambient temperature, after which the components of phase B are added with stirring to phase A.

9. Lipstick (Anhydrous)

|  | % |
|---|---|
| Castor oil | 27.45 |
| Compound of Example 2 | 30.5 |
| Beeswax | 10.5 |
| Candelilla wax | 7.5 |
| Ozocerite | 5.5 |
| Isopropyl lanolate | 5 |
| Colourants | 13.55 |
|  | 100 |

All the cosmetic products of Examples 3 to 9 were tested and showed high stability for 3 months at temperatures of 23° C., 37° C. and 47° C.

They have good organoleptic properties, namely:

Both the emulsions and the anhydrous products are homogeneous, fine, smooth and bright.

We claim:

1. A cosmetic composition comprising a water-in-oil emulsion having a fatty phase containing fatty acid diesters of 2,3-butanediol.

2. A cosmetic composition comprising an oil-in-water emulsion having a fatty phase containing fatty acid diesters of 2,3-butanediol.

3. An anhydrous cosmetic composition comprising a fatty phase containing fatty acid diesters of 2,3-butanediol.

4. A composition according to claim 1, 2 or 3 wherein 2,3-butanediol is esterified with fatty acids selected from the group consisting of $C_{12-22}$ fatty acids.

5. A composition according to claim 1, 2 or 3 wherein 2,3-butanediol is esterified with fatty acids selected from the group consisting of $C_{16-22}$ fatty acids.

6. A composition according to claim 1, 2 or 3 wherein the diesters are present in an amount of from 0.5% to 80% by weight based on the weight of the composition.

7. A composition according to claim 1 or 2 wherein the composition contains an emulsifier in an amount of from 1% to 20% by weight based on the weight of the composition.

8. A composition according to claim 1 or 2 wherein the diesters are present in an amount of from 0.5% to 20% by weight based on the weight of the composition.

9. A composition according to claim 3 wherein the diesters are present in an amount of from 10% to 80% by weight based on the weight of the composition.

10. A composition according to claim 3 wherein the diesters are present in an amount of from 10% to 40% by weight based on the weight of the composition.

11. A composition according to claim 3 further comprising waxes in an amount of from 5% to 30% by weight based on the weight of the composition.

12. A composition according to claim 1, 2 or 3 further comprising an antioxidant in an amount of from 0.02% to 0.2% by weight based on the weight of the composition.

13. A composition according to claim 1, 2 or 3 further comprising an ultraviolet filter.

14. A composition according to claim 1, 2 or 3 further comprising a perfume.

15. A composition according to claim 1, 2 or 3 further comprising a member selected from the group consisting of waxes, long-chain alcohols and thickening agents.

16. A composition according to claim 2 which is a shampoo.

17. A composition according to claim 3 which is a lipstick.

* * * * *